(12) United States Patent
Arciero et al.

(10) Patent No.: US 11,911,047 B2
(45) Date of Patent: Feb. 27, 2024

(54) ADJUSTABLE DRILL GUIDE AND METHODS OF USE THEREOF

(71) Applicants: Smith & Nephew, Inc., Memphis, TN (US); Smith & Nephew Orthopaedics AG, Zug (CH); Smith & Nephew Asia Pacific Pte. Limited, Singapore (SG); Robert Arciero, Farmington, CT (US)

(72) Inventors: Robert Arciero, Farmington, CT (US); Oliver Streit, Tuttlingen (DE); Dirk Wunderle, Zurich (CH); Alex Seidl, Zurich (CH)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 337 days.

(21) Appl. No.: 17/505,856

(22) Filed: Oct. 20, 2021

(65) Prior Publication Data

US 2022/0039809 A1 Feb. 10, 2022

Related U.S. Application Data

(62) Division of application No. 16/931,538, filed on Jul. 17, 2020, now Pat. No. 11,172,943.

(60) Provisional application No. 62/876,031, filed on Jul. 19, 2019.

(51) Int. Cl.
*A61B 17/17* (2006.01)
*A61B 17/16* (2006.01)
*A61B 17/00* (2006.01)

(52) U.S. Cl.
CPC .......... *A61B 17/17* (2013.01); *A61B 17/1626* (2013.01); *A61B 17/1778* (2016.11); *A61B 17/1796* (2013.01); *A61B 2017/00389* (2013.01); *A61B 2017/00398* (2013.01)

(58) Field of Classification Search
CPC ........................... A61B 17/1778; A61B 17/17
See application file for complete search history.

(56) References Cited

U.S. PATENT DOCUMENTS

| | | | | |
|---|---|---|---|---|
| 4,708,139 A | * | 11/1987 | Dunbar, IV | A61B 17/1764 D24/140 |
| 4,739,751 A | * | 4/1988 | Sapega | A61B 17/1764 606/88 |
| 5,300,077 A | * | 4/1994 | Howell | A61B 17/1764 606/98 |

(Continued)

OTHER PUBLICATIONS

Application No. 20186416.2-1122 Examination Report dated Feb. 3, 2023.

*Primary Examiner* — Christian A Sevilla
(74) *Attorney, Agent, or Firm* — Burns & Levinson, LLP; Joseph M. Maraia; Marlo Schepper Grolnic

(57) ABSTRACT

Drill guide assemblies are adjustable for proper alignment of drill holes in the glenoid with the drill holes in the coracoid during a Latarjet procedure. The drill guide has an aimer arm extending from the body of the drill guide which has a fixed angle with respect to a drill sleeve inserted through the guide. The aimer arm can move up or down relative to the drill sleeve while maintaining the fixed angle relative to the drill sleeve by actuation of a translation member on the body.

15 Claims, 7 Drawing Sheets

(56) References Cited

U.S. PATENT DOCUMENTS

| | | | |
|---|---|---|---|
| 2012/0123417 A1* | 5/2012 | Smith | A61B 17/1714 606/98 |
| 2014/0228848 A1* | 8/2014 | Torrie | A61B 17/17 606/80 |
| 2016/0089159 A1* | 3/2016 | Ardito | A61B 17/1714 606/96 |
| 2017/0112625 A1* | 4/2017 | Taverna | A61B 17/1778 |
| 2017/0252048 A1* | 9/2017 | Sauer | A61B 17/1714 |

* cited by examiner

ADJUSTABLE DRILL GUIDE AND METHODS OF USE THEREOF

CROSS-REFERENCE TO RELATED APPLICATIONS

This application is a divisional of U.S. application Ser. No. 16/931,538, filed Jul. 17, 2020, entitled ADJUSTABLE DRILL GUIDE AND METHODS OF USE THEREOF, which in turn claims priority to and benefit of U.S. Provisional Application No. 62/876,031, filed Jul. 19, 2019, the contents of which are incorporated herein by reference in their entirety for all purposes.

FIELD

The present disclosure relates generally to surgical drill guides. More specifically, the present disclosure relates to adjustable drill guide assemblies for the positioning and orienting of bone tunnels to be drilled in a glenoid bone.

BACKGROUND

A Latarjet operation, also known as the Latarjet-Bristow procedure, is a surgical procedure used to treat recurrent shoulder dislocations, typically caused by bone loss or a fracture of the glenoid. The Latarjet procedure typically involves the removal and transfer of a section of the coracoid process, as well as its attached soft tissue, to the glenoid cavity. This placement of the coracoid acts as a bone block which, combined with the transferred soft tissue, prevents further dislocation of the joint. During the procedure, holes are generally drilled through both of the coracoid and the glenoid through which screws or sutures attached to anchors or buttons can be placed for securing the section of the coracoid to the glenoid.

Surgical drill guides can be used to place the holes in the glenoid neck at a fixed distance from the glenoid articulating surface to align with the drill holes of the coracoid. However, misalignment between the two sets of holes can occur. When the holes are misaligned, the suture/anchor or button constructs generally allow some tolerance in aligning the coracoid flush to the glenoid surface, because the suture has play within the drill holes. However, when a surgeon wants to use screws instead of the suture/anchor or button construct, retroactive alignment is not possible once the holes are drilled. Surgeons generally address the misalignment by shaving down the thickness of the coracoid with a burr. However, use of a burr can potentially cause cartilage damage and affect the accuracy of the surface alignment between the glenoid and the coracoid, as well as affecting surface quality.

SUMMARY

Described herein is a drill guide assembly in which the drill guide is adjustable for properly aligning the holes in the glenoid with the holes in the coracoid in a Latarjet procedure. The drill guide has an aimer arm extending from the body of the drill guide which has a fixed angle with respect to a drill sleeve inserted through the guide. The aimer arm can move up or down relative to the drill sleeve while maintaining the fixed angle relative to the drill sleeve by actuation of a translation member on the body. The aimer arm can move in a stepped fashion in 1 mm increments, or in a non-stepped fashion. A locking knob on the aimer arm can be used to lock the aimer arm at the desired position. Advantageously, the component parts of the drill guide assembly can be disassembled for cleaning.

Examples of the drill guide assembly of this disclosure may include one or more of the following, in any suitable combination.

In examples, a drill guide assembly of this disclosure includes an elongate body including a proximal end, a distal end and a longitudinal axis extending between the proximal and distal ends. At least one channel extends along the longitudinal axis of the body from the proximal end to the distal end. A sleeve is slidably disposed within the at least one channel. A distal end of the sleeve is configured to be secured to a first surface of a bone. An aimer arm extends distally from the body. A distal end of the aimer arm is configured to be secured to a second surface of the bone. The aimer arm extends at a fixed angle with respect to the sleeve. A vertical distance between the aimer arm and the sleeve is adjustable to a pre-selected distance by actuation of a translation member on the body such that the aimer arm maintains the fixed angle with respect to the sleeve.

In examples, the assembly further includes a handle extending from a lower surface of the body configured to be held by a user. In examples, the preselected distance is between 6 mm and 9 mm. In examples, the at least one channel is two channels extending on opposing sides of the aimer arm, and a distance between the two channels is about 10 mm. In examples, the sleeve includes a bore extending from a proximal end to a distal end of the sleeve for the passage of a drill. In examples, the assembly further includes a locking mechanism for locking the sleeve at a predetermined position within the at least one channel. In examples, the proximal end of the sleeve includes a depth stop. A diameter of the depth stop selected to be larger than a diameter of the channel for limiting distal movement of the sleeve within the channel. In examples, the fixed angle is 10°. In examples, the distance between the aimer arm and the sleeve is adjustable in a stepped or a non-stepped manner. In examples, the assembly further includes an alignment member extending from an upper surface of the body adjacent the distal end of the body. The alignment member defines a plurality of longitudinal slots. In examples, the translation member is a rotatable wheel. In examples, the aimer arm extends through opposing ones of the plurality of slots along the longitudinal axis. A projection of the aimer arm is configured to serially engage the rotatable wheel such that the distance between the aimer arm and the sleeve is adjustable by rotation of the rotatable wheel by 90°. In examples, a pivot point of the rotatable wheel is offset from a center of the rotatable wheel in both a horizontal and a vertical direction. In examples, a proximal end of the aimer arm includes a locking knob for securing the aimer arm against the alignment member at the preselected distance. In examples, the assembly further includes a compression spring disposed within the alignment member for biasing the projection of the aimer arm against the rotatable wheel.

Examples of a method for positioning a bone tunnel in bone of this disclosure include positioning a distal tip of an aimer arm of a drill guide assembly against a first surface of a bone. The drill guide assembly includes an elongate body including a proximal end, a distal end and a longitudinal axis extending between the proximal and distal ends. At least one channel extends along the longitudinal axis of the body from the proximal end to the distal end. A sleeve is slidably disposed within the at least one channel. A distal end of the sleeve is configured to be secured to a second surface of the bone. The aimer arm extends from the body at a fixed angle with respect to the sleeve. The method also includes advancing the sleeve through the at least one channel, whereby the bone is fixed between the distal tip of the aimer arm and the distal end of the sleeve. The method also includes actuating a translation member on the body such that a vertical distance between the aimer arm and the sleeve is adjusted to a preselected distance while maintaining the fixed angle with respect to the sleeve.

In further examples, the translation member is a rotatable wheel, and actuating the translation member includes rotating the rotatable wheel by 90°. In examples, the method also includes locking the aimer arm at the preselected distance. In examples, the vertical distance between the aimer arm and the drill sleeve is adjusted in a stepped or a non-stepped manner. In examples, the method further includes locking the sleeve within the channel at a preselected position with a locking mechanism. In examples, the fixed angle is 10°. In examples, the preselected distance is between 6 mm and 9 mm.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1A:
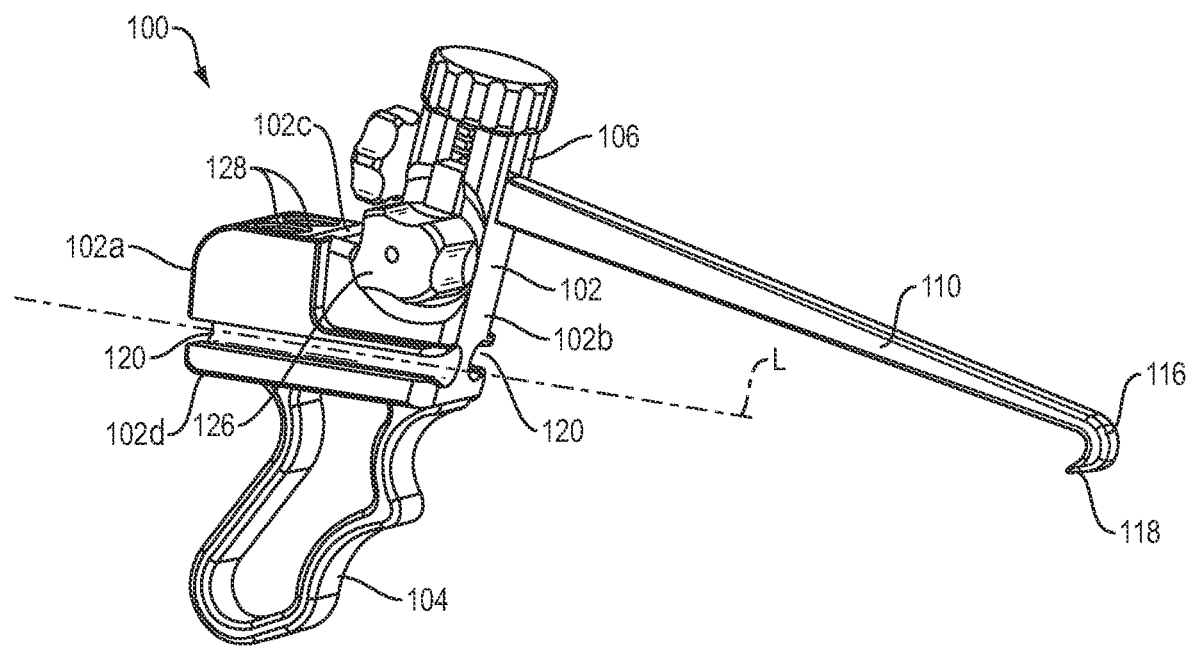
FIGS. 1A and 1B are perspective views of an exemplary drill guide assembly of this disclosure.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts. Use of the terms "upper," "lower," and the like is intended only to help in the clear description of the present disclosure and are not intended to limit the structure, positioning and/or operation of the disclosure in any manner.

Referring now to FIG. 1A, an exemplary drill guide assembly 100 of this disclosure is shown in a perspective view. The assembly 100 includes a guide body 102 having a proximal end 102*a* and a distal end 102*b*. An upper surface 102*c* and a lower surface 102*d* extend between the proximal end 102*a* and the distal end 102*b* of the body 102. A handle 104 extends from the lower surface 102*d* of the body 102 and is configured to be held by a user in a "pistol-style" configuration. In alternative examples, not shown, the handle 104 is an in-line handle, formed substantially coaxially with the body 102. The body 102 further includes at least one cylindrical channel 120 extending from the proximal end 102*a* to the distal end 102*b* of the body 102 for slidably receiving an elongate drill sleeve 134 (FIG. 1D). The drill sleeve 134 is configured for the passage of a guidewire (not shown) for locating the bone tunnels to be drilled in the bone. In the example of FIG. 1A, two channels 120 are defined on opposite sides of the body 102 configured for positioning two parallel bone tunnels through the bone. In examples, a distance between the channels 120 is about 10 mm, ensuring accurate and consistent placement of the bone tunnels about 10 mm apart within the bone. An elongate aimer arm 110 extends distally from the body 102 at about a 10° angle toward the longitudinal axis L of a path defined by the channels 120 for insertion of the drill sleeve 134. The aimer arm 110 includes a distal tip 116 with a spiked hook 118 which is configured to contact a bone surface. In alternative examples, not shown, the distal tip 116 could be pointed or comprise a blunted end, such as a spherical tip. The assembly 100 is configured such that a vertical distance between the aimer arm 110 and the drill sleeve 134 is adjustable based on a pre-measured thickness of the bone to be drilled by actuation of a translation member on the body, such as a rotatable wheel 126, while still maintaining the 10° angle between the aimer arm 110 and the drill sleeve 134. The upper surface 102*c* of the body 102 also includes at least one threaded opening 128 adjacent the proximal end 102*a* for receiving a threaded ratchet pawl (not shown) for locking the drill sleeve 134 within the channel 120 at a desired position.

Figure 1B:
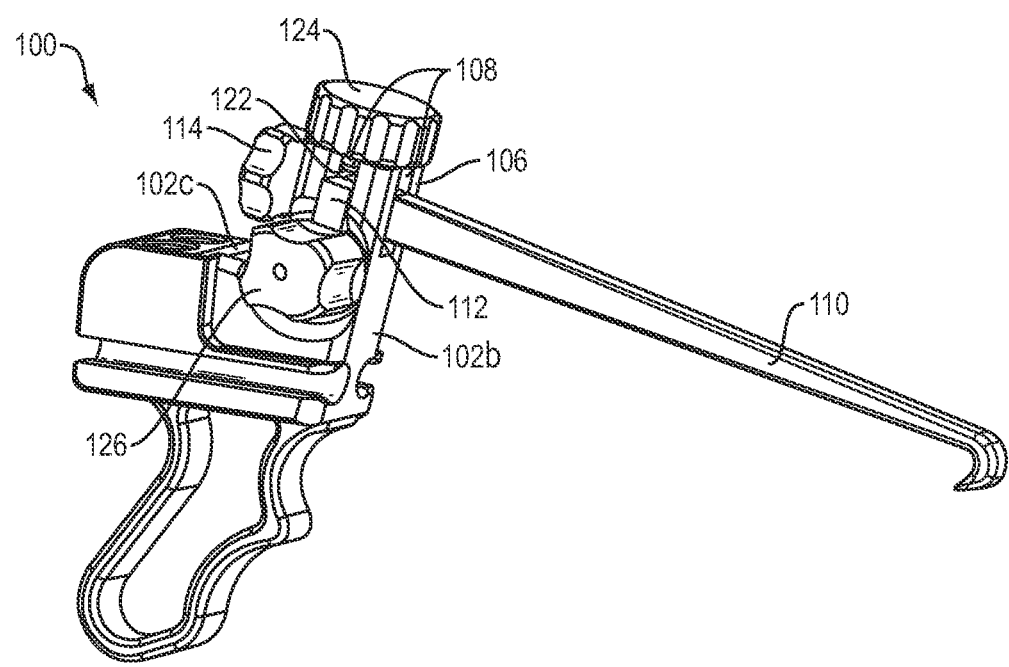

Turning now to FIG. 1B, in the example of the assembly 100, an alignment member 106 extends from the upper surface 102*c* of the body 102 adjacent the distal end 102*b*. The alignment member 106 defines a plurality of longitudinal slots 108 within the alignment member 106. The aimer arm 110 extends through opposing slots 108 along the longitudinal axis and is vertically moveable within the slots 108 relative to the drill sleeve 134. A proximal end of the aimer arm 110 includes a locking knob 114 which can be used to secure the aimer arm 110 in the desired vertical position within the slots 108. A projection 112 on the aimer arm 110 extends through a third slot 108 and is configured to serially engage a flat edge of the rotatable wheel 126, as further described below. A compression spring 122 is disposed within the alignment member 106 between the aimer arm 110 and an upper knob 124. The spring 122 is configured to bias the projection 112 of the aimer arm 110 against the rotatable wheel 126. In FIG. 1B, the rotatable wheel 126 is shown rotated 90° from the position of the rotatable wheel 126 shown in FIG. 1A. In FIG. 1B, the spring 122 is also shown as more compressed and the aimer arm 110 in a higher vertical position than the spring 122 and the aimer arm 110 of FIG. 1A.

Figure 1C:
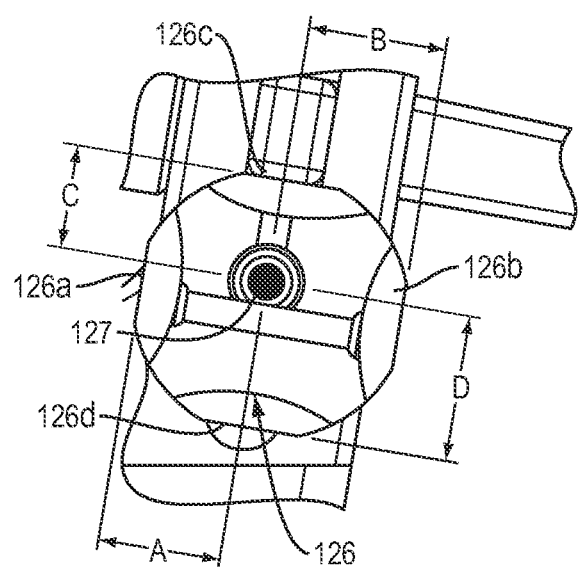
FIG. 1C is a detailed view of the side wheel of the drill guide assembly of FIGS. 1A and 1B.
Figure 1D:
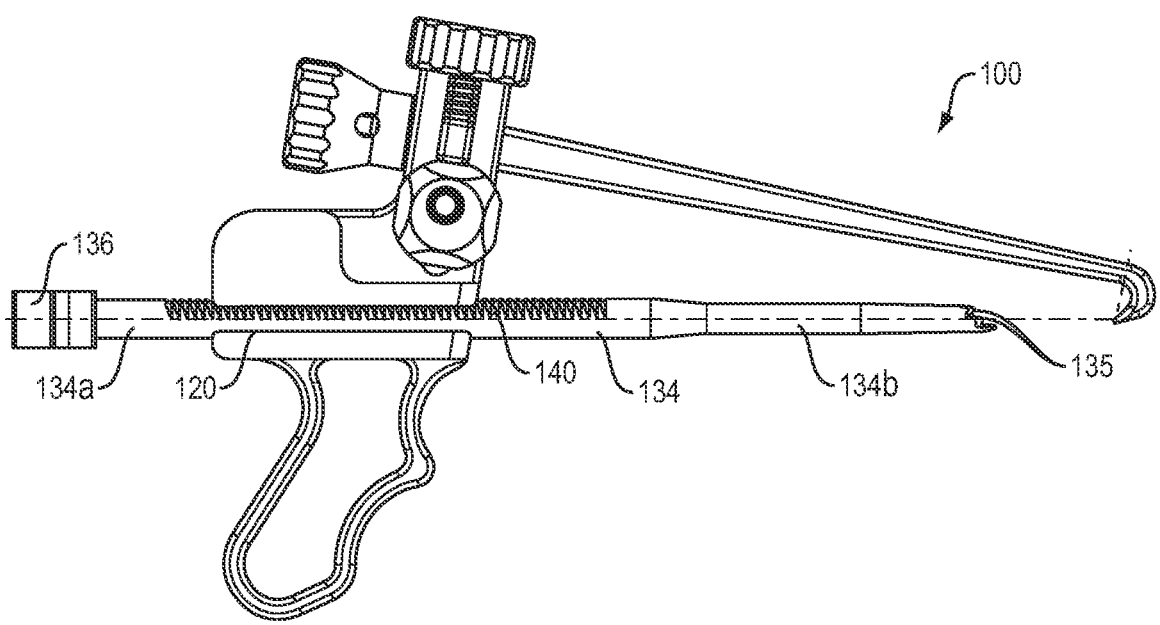
FIG. 1D is an assembled view of the drill guide assembly of this disclosure.

Turning now to FIG. 1C, the rotatable wheel 126 includes a pivot point 127 that is offset from the center of the rotatable wheel 126 in both a horizontal and vertical direction. For example, the pivot point 127 may be disposed at a first distance A from a first flat edge 126a of the rotatable wheel 126 selected to be smaller than a second distance B from a second flat edge 126b of the rotatable wheel 126 in a horizontal direction. In examples, the first distance A may be 8 mm and second distance B may be 9 mm. Similarly, the pivot point 127 may be disposed at a third distance C from a third flat edge 126c of the rotatable wheel 126 selected to be smaller than a fourth distance D from a fourth flat edge 126d of the rotatable wheel 126 in a vertical direction. In examples, the third distance C may be 7 mm and the fourth distance D may be 10 mm. In this manner, by a 90° rotation of the rotatable wheel 126, the distance between the aimer arm 110 and the drill sleeve 134 may be adjusted in a stepped manner in 1 mm increments from about 6 mm to about 9 mm.

Turning now to FIG. 1D, the drill guide assembly 100 is shown with drill sleeves 134 inserted through the channels 120. Each drill sleeve 134 includes a depth stop 136 at a proximal end of the drill sleeve 134. The depth stop 136 can be used by a surgeon to grasp and manipulate the drill sleeve 134 during surgery. The depth stop 136 has a larger outer diameter than that of the channel 120, such that when drill sleeve 134 is inserted through the channel 120, the depth stop 136 prevents drill sleeve 134 from being inserted completely through the channel 120. The distal end of the drill sleeve 134 may be angled and include a plurality of teeth 135 for securing the drill sleeve 134 against bone. A diameter of a proximal portion 134a of the drill sleeve 134 is selected to be larger than a diameter of a distal portion 134b of the drill sleeve 134. The drill sleeve 134 has a cylindrical bore 138 (FIG. 2A) extending through the drill sleeve 134 which provides a passageway for a guidewire (not shown). The proximal portion 134a of the drill sleeve 134 also includes a rack 140 in the form of a series of ratchet teeth or radial grooves along one side of drill sleeve 134. A ratchet pawl 130 (FIG. 2A) is configured to engage with the rack 140 and lock the drill sleeve 134 in a desired position within channel 120.

Figure 2:
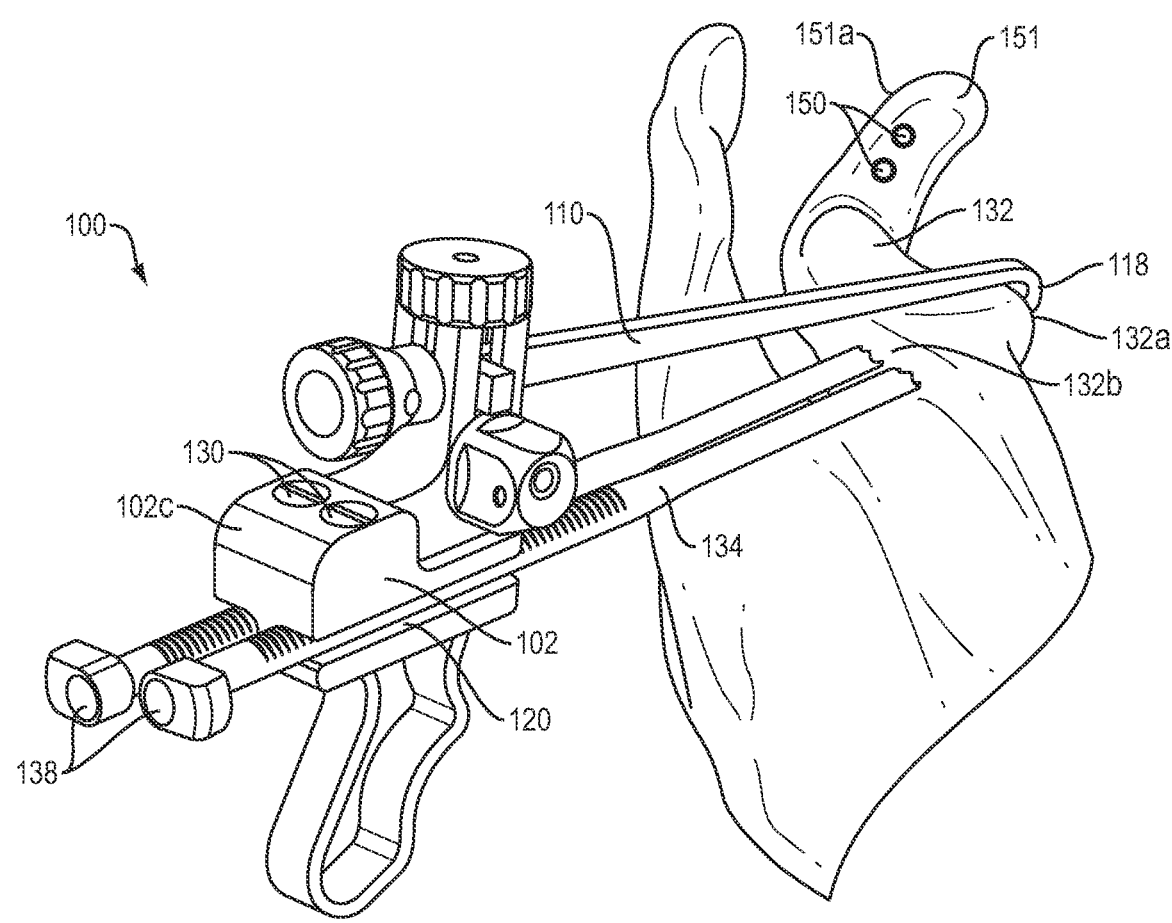
FIG. 2 illustrates the use of the drill guide assembly of this disclosure.

The use of the drill guide assembly 100 will now be described with reference to FIG. 2. The glenoid 132 may be initially prepared for the procedure by rasping the inferior surface 132a of the glenoid 132 for better attachment to the coracoid. Initially, drill holes 150 are drilled in a center of the coracoid 151 at a distance from the lateral border 151a (typically 5 to 9 mm from the lateral border 151a, depending on the width of the coracoid 151). The distance of the drill holes 150 to the lateral border 151a of the coracoid 151 is measured and the result is used to set the pre-selected distance of the aimer arm 110 from the drill sleeve 134. For example, if the distance of the drill holes 150 from the lateral border 151a of the coracoid 151 is 6 mm, the distance of the aimer arm 110 from the drill sleeve 134 is selected to be 6 mm. After an incision is made to introduce the assembly 100 into the patient's shoulder, the surgeon adjusts the orientation of aimer arm 110 until the hook 118 is placed on the inferior surface 132a of the glenoid 132 to hold the aimer arm 110 in place, making sure that the under surface of the aimer arm 110 is in full contact with glenoid cartilage. The drill sleeve 134 is then inserted through channel 120 of the assembly 100 so that the distal tip of the drill sleeve 134 is flush against the anterior surface 132b of the glenoid 132. The drill sleeve 134 is then locked into the channel 120 by the ratchet pawl 130. Subsequently, a drill (not shown) is inserted through the bore 138 of the drill sleeve 134 and drilled through the glenoid 132. The assembly 100 is then removed from the patient's shoulder.

Figure 3:
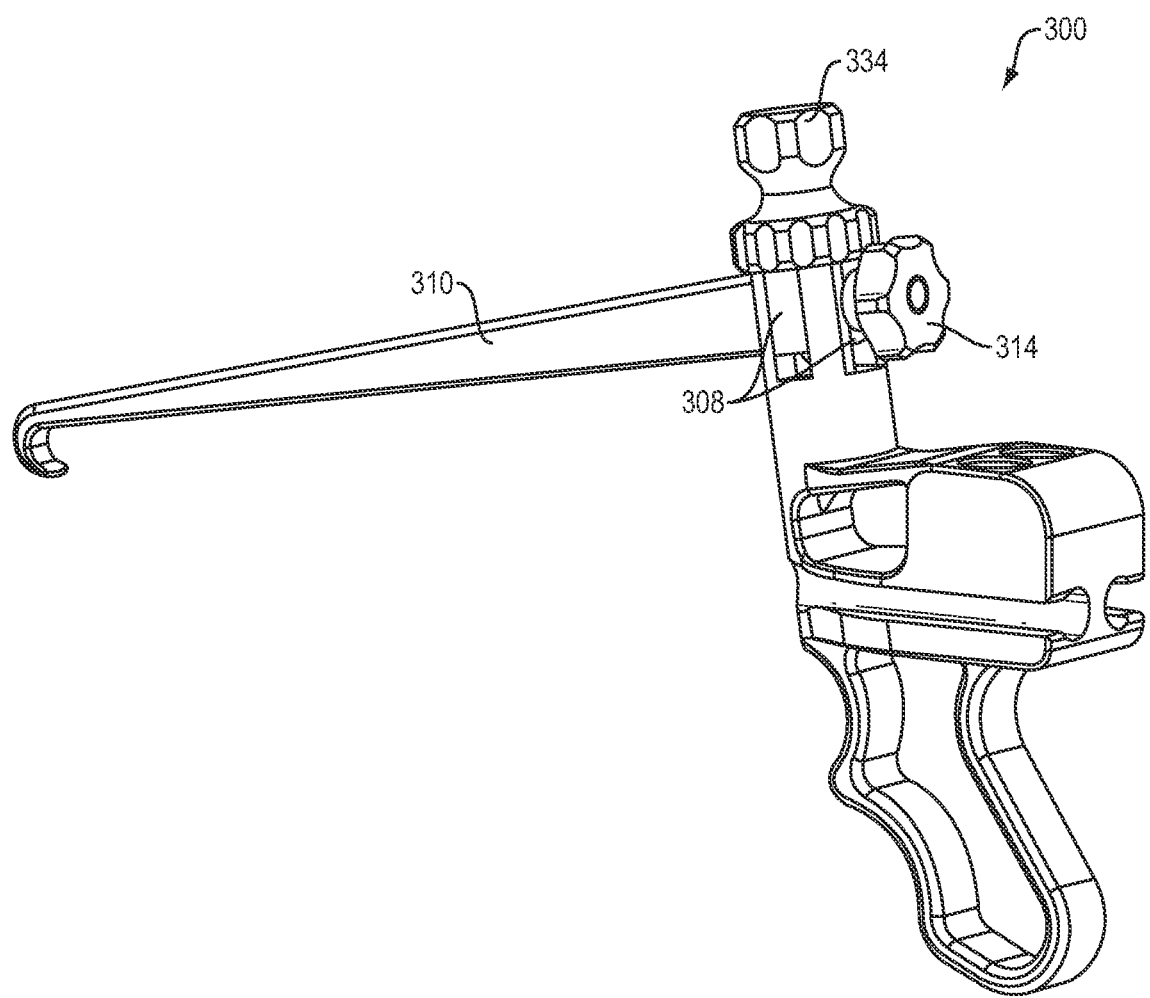
FIG. 3 illustrates an alternative example of the drill guide assembly of this disclosure.
Figure 4A:
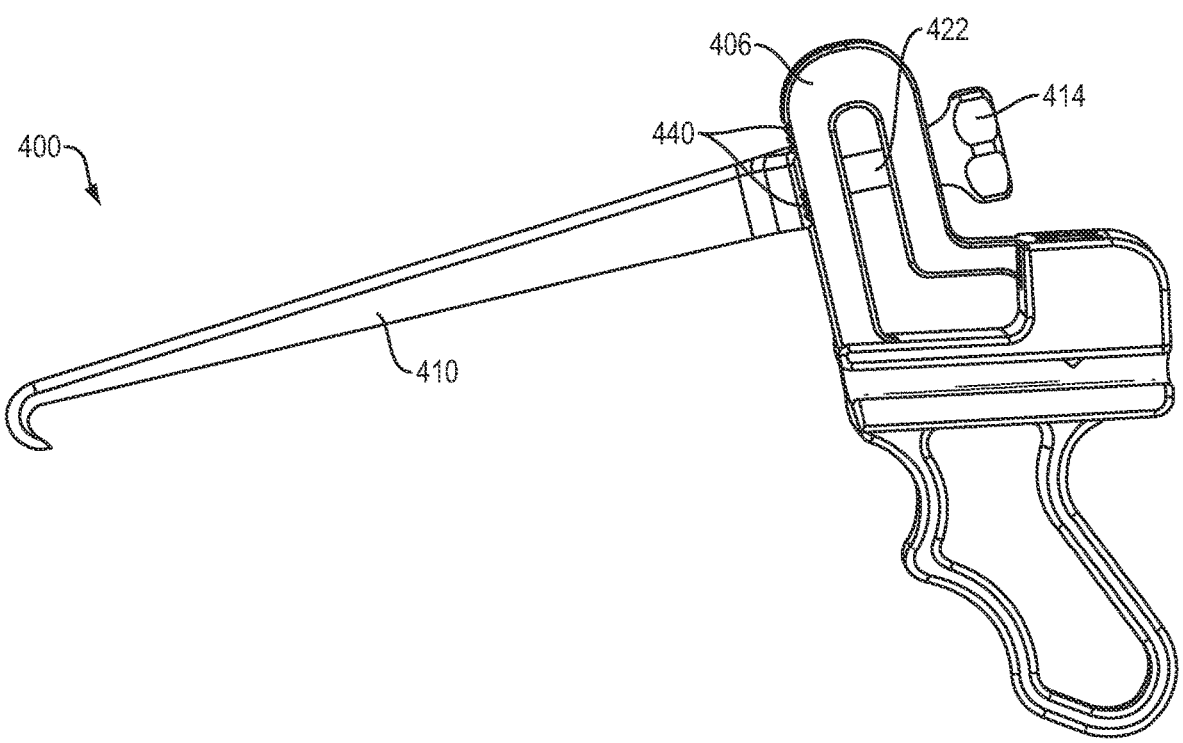
FIGS. 4A and 4B illustrate another alternative example of the drill guide assembly of this disclosure.
Figure 4B:
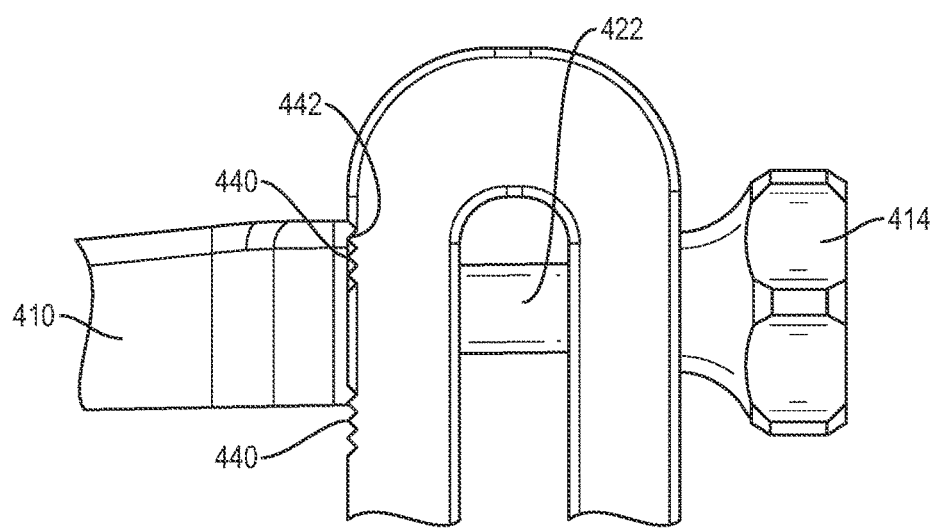

An alternative example of a drill guide assembly 300 is shown in FIG. 3. In the example of FIG. 3, a spring-loaded top knob 334 is used to adjust the height of the aimer arm 310 within the slots 308 in a non-stepped manner. The locking knob 314 is used to lock the height of the aimer arm 310 in place. In an alternative example of a drill guide assembly 400, shown in FIGS. 4A and 4B, the alignment member 406 includes a first plurality of teeth 440 spaced apart at a distance of about 1 mm. The plurality of teeth 440 are configured to engage a second plurality of teeth 442 (FIG. 4B) on the aimer arm 410 so that the height of the aimer arm 410 can be adjusted by 1 mm increments. A spring 422 is disposed within the alignment member 406 to ease the adjustment of the aimer arm 410. The locking knob 414 is used to lock the height of the aimer arm 410 in place.

Figure 5:
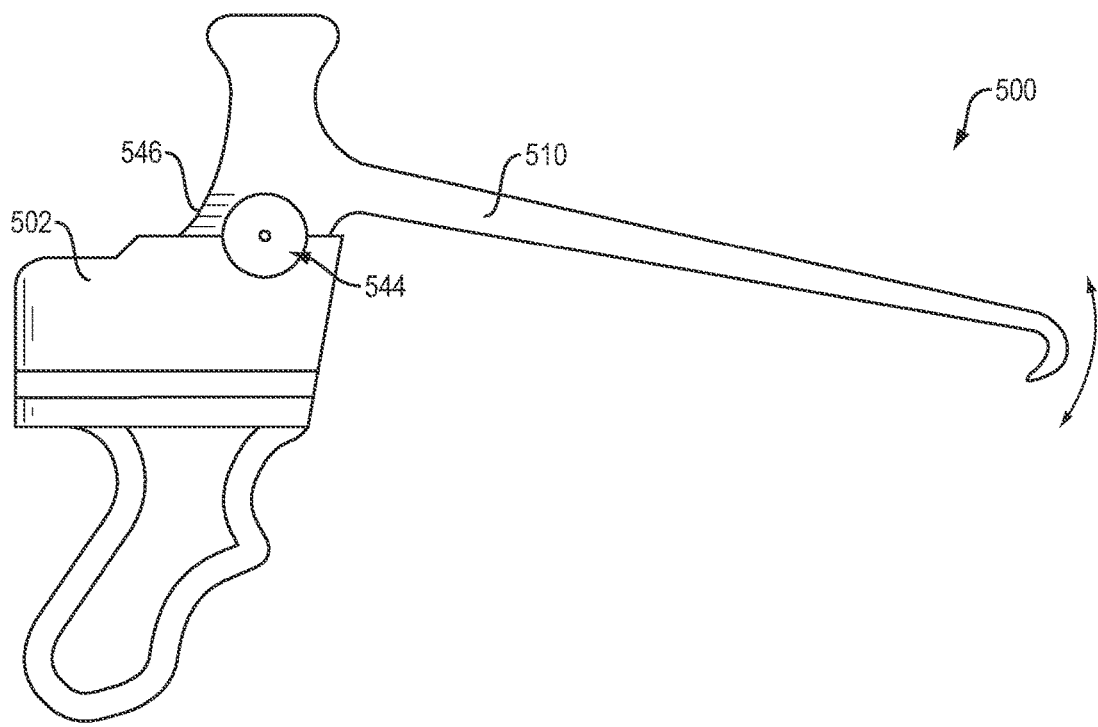
FIG. 5 illustrates another alternative example of the drill guide assembly of this disclosure.

Another example of a drill guide assembly 500 is shown in FIG. 5. In the example of FIG. 5, the aimer arm 510 is connected via a rotatable joint 544 to the guide body 502. The height of the aimer arm 510 is adjusted by moving the aimer arm 510 up or down relative to the guide body 502. A scale 546 on the guide body 502 would indicate the degree of adjustment in millimeters. The joint 544 could include a lock mechanism (e.g., a thumb wheel) to lock the aimer arm 510 at the desired height.

Figures 6A, 6B:
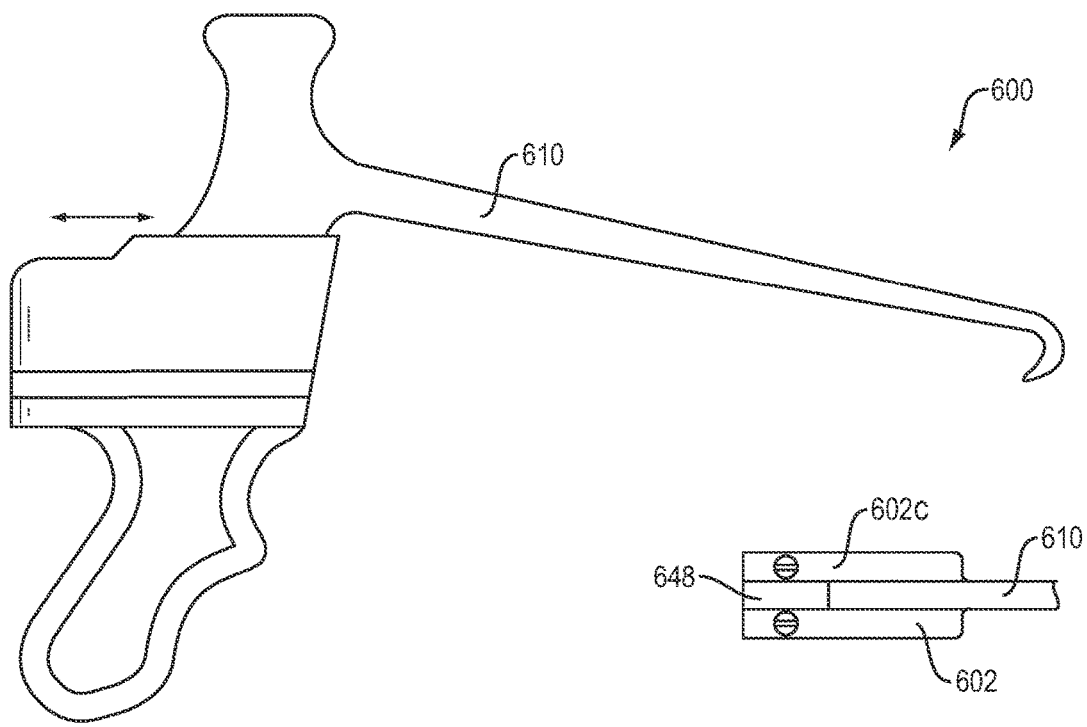
FIGS. 6A and 6B illustrate yet another alternative example of the drill guide assembly of this disclosure.
Figure 7:
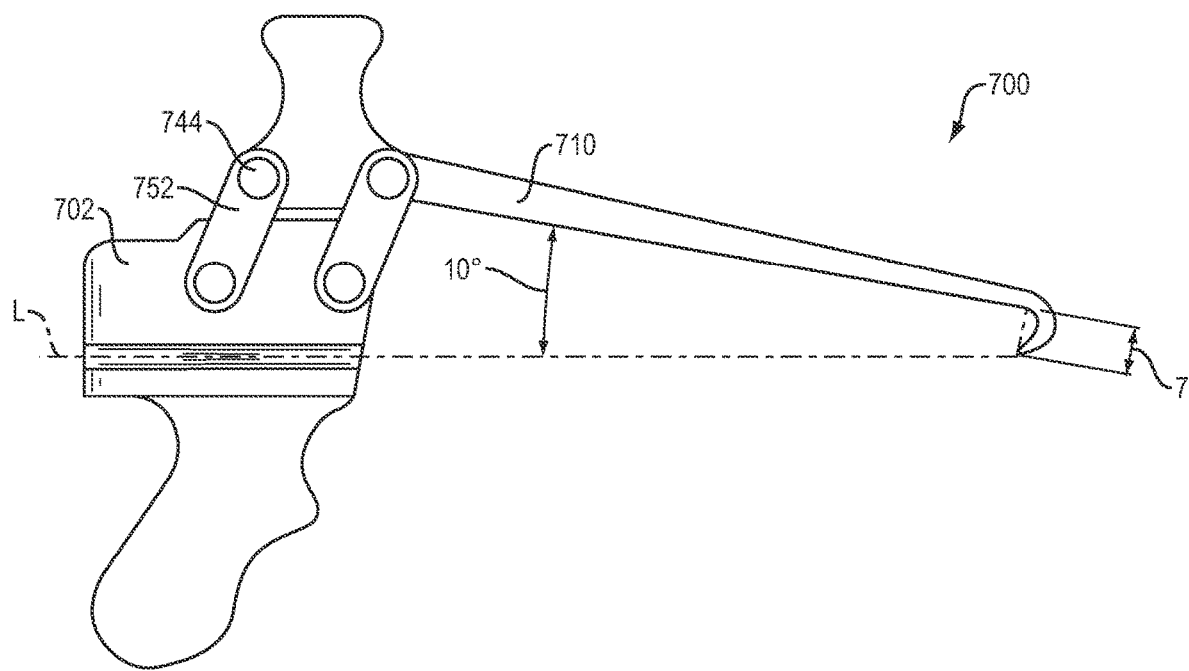
FIG. 7 illustrates another alternative example of the drill guide assembly of this disclosure.

An alternative example of a drill guide assembly 600 is shown in FIGS. 6A and 6B. In the example of FIGS. 6A and 6B, a plurality of aimer arms 610 having different heights (e.g., 5 mm, 6 mm, 7 mm and 8 mm) could be configured to slide into a T-shaped slot 648 on a top surface 602c of the guide body 602. A locking mechanism, such as a thumb wheel or a click mechanism, would secure the aimer arm 610 in place. An alternative example of a drill guide assembly 700, shown in FIG. 7, uses a parallelogram joint configuration. In the example of FIG. 7, the fixed angle of the joint 744 is kept constant relative to the longitudinal axis L of the drill sleeve for all offsets. The aimer arm 710 is connected via the joints 744 and the lever arms 752 to the guide body 702 and a height of the aimer arm 710 can be adjusted by moving the aimer arm 710 up and down relative to the body 702. An additional device (for example, a screw, an excenter, etc.), along with a scale on the guide body 702, could be used to adjust the aimer arm 710 in a stepped or non-stepped manner.

One skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

What is claimed is:

1. A method for positioning a bone tunnel in bone comprising:
 positioning a distal tip of an aimer arm of a drill guide assembly against a first surface of a bone, the drill guide assembly comprising:
  an elongate body including a proximal end, a distal end and a longitudinal axis extending between the proximal and distal ends;
  at least one channel extending along the longitudinal axis of the body from the proximal end to the distal end; and
  a sleeve slidably disposed within the at least one channel, a distal end of the sleeve configured to be secured to a second surface of the bone;
  wherein the aimer arm extends from the body at a fixed angle with respect to the sleeve;
 advancing the sleeve through the at least one channel, whereby the bone is fixed between the distal tip of the aimer arm and the distal end of the sleeve; and
 actuating a translation member on the body such that a vertical distance between the aimer arm and the sleeve is adjusted to a preselected distance while maintaining the fixed angle with respect to the sleeve.

2. The method of claim 1, wherein the translation member is a rotatable wheel, and wherein the actuating the translation member comprises rotating the rotatable wheel by 90°.

3. The method of claim 1, further comprising locking the aimer arm at the preselected distance.

4. The method of claim 1, wherein the vertical distance between the aimer arm and the drill sleeve is adjusted in a stepped or a non-stepped manner.

5. The method of claim 1, further comprising locking the sleeve within the at least one channel at a preselected position with a locking mechanism.

6. The method of claim 1, wherein the fixed angle is 10°.

7. The method of claim 1, wherein the preselected distance is between 6 mm and 9 mm.

8. The method of claim 1, wherein positioning the distal tip of the aimer arm of the drill guide assembly comprises positioning with a handle extending from a lower surface of the body.

9. The method of claim 1, wherein the at least one channel is two channels extending on opposing sides of the aimer arm, and wherein a distance between the two channels is about 10 mm.

10. The method of claim 1, wherein the sleeve comprises a bore extending from a proximal end to a distal end of the sleeve for passage of a drill.

11. The method of claim 1, wherein a proximal end of the sleeve comprises a depth stop, a diameter of the depth stop selected to be larger than a diameter of the at least one channel for limiting distal movement of the sleeve within the at least one channel.

12. The method of claim 2, further comprising an alignment member extending from an upper surface of the body adjacent the distal end of the body, the alignment member defining a plurality of longitudinal slots;
 wherein the aimer arm extends through opposing ones of the plurality of slots along the longitudinal axis, a projection of the aimer arm configured to serially engage the rotatable wheel such that the distance between the aimer arm and the sleeve is adjustable by rotation of the rotatable wheel by 90°.

13. The method of claim 12, wherein a pivot point of the rotatable wheel is offset from a center of the rotatable wheel in both a horizontal and a vertical direction.

14. The method of claim 12, further comprising securing the aimer arm against the alignment member at the preselected distance.

15. The method of claim 12, wherein the projection of the aimer arm is biased against the rotatable wheel by a compression spring disposed within the alignment member.

* * * * *